United States Patent [19]

Kameny

[11] 4,014,345
[45] Mar. 29, 1977

[54] ELECTRODE

[76] Inventor: Stanley L. Kameny, 14314 Hatteras St., Van Nuys, Calif. 91401

[22] Filed: Oct. 28, 1975

[21] Appl. No.: 625,935

[52] U.S. Cl. ............................................... 128/417
[51] Int. Cl.$^2$ .......................................... A61N 1/04
[58] Field of Search .......... 128/417, 404, 410, 411, 128/416, 418, 2.06 E, 2.1 E, DIG. 4

[56] References Cited

UNITED STATES PATENTS

| 1,583,087 | 5/1926 | Morse | 128/417 |
|---|---|---|---|
| 2,651,304 | 9/1953 | Browner | 128/417 |
| 3,085,577 | 4/1963 | Berman et al. | 128/418 |
| 3,279,468 | 10/1966 | LeVine | 128/410 |
| 3,545,432 | 12/1970 | Berman | 128/2.06 E |
| 3,830,229 | 8/1974 | Johnson | 128/417 |
| 3,865,099 | 2/1975 | Robichaud | 128/417 |
| 3,882,853 | 5/1975 | Gofman et al. | 128/2.06 E |

*Primary Examiner*—Robert W. Michell
*Assistant Examiner*—Lee S. Cohen
*Attorney, Agent, or Firm*—Harvey S. Hertz

[57] ABSTRACT

An electrode for applying electrical signals to a human body from a signal generator. The electrode comprises a retaining ring formed of insulating material. The retaining ring has a rear wall integral with one end of a side wall with an opening formed in the rear wall. An inwardly extending lip is integral with the other end of the side wall and defines a front opening. An inwardly extending flange integral with and extending from the junction of the rear and side walls is generally parallel to the and spaced intermediate the lip and the rear wall to define an enlarged height annular groove and a reduced height annular groove adjacent the lip and the rear wall, respectively. A generally planar conductive plate having a first side surface and a second side surface is dimensioned to be inserted in the reduced height groove and retained therein. An electrical connector member is secured to the conductive plate first side surface and extends into the retaining ring rear wall opening. A sponge member has a thickness approximately equal to the height of the enlarged height groove enabling the sponge to be retained in the enlarged height groove. The sponge when wet is juxtaposed with the conductive plate second side surface and extends into the front wall opening of the insulative retaining ring. The retaining ring avoids corrosion by separating wet and dry portions of the electrode.

1 Claim, 5 Drawing Figures

ELECTRODE

BACKGROUND OF THE INVENTION

1. Field of the Invention

The field of art to which the invention pertains includes the field of electrodes, particularly, to an electrode whose members can be easily assembled in an insulative retaining ring.

2. Description of the Prior Art

Conventional electrode structures for either applying electrical signals to a body or for receiving signals from the body when placed in direct contact with the body, have been found to provide poor electrical connection between the lead connecting the electrode to the signal generator or measuring instrument. In one prior art embodiment the lead is soldered to the electrode, and it has been found that due to electrolytic action in the presence of a liquid, corrosion can occur, resulting in eventual breakdown of the connection, or of the connecting lead. In this construction, the lead connections normally are fitted into a side opening in the electrode requiring a structural opening in the side of the electrode structure. The side opening required in this construction prevents sealing of the lead cable from the liquid. In other prior art structures, a connector is brought out of the rear of the electrode structure. However, a portion of the connector structure is immersed in a fluid portion of the electrode and, thus, is subject to corrosion. Other electrode lead connections have also been found to corrode where metal such as aluminum foil is used to form the lead terminal on the electrode. Still other leads utilize conductive silicone rubber which tends to break down after use so as to cause an uneven current distribution.

The present invention provides a novel electrode insulative structure which simultaneously positions portions of the electrode structure in place and provides a good seal therewith. Portions of the electrode structure are also easily replaceable. An electrical connector member is soldered directly to a conductive plate and corrosive action is minimized. Portions of the electrode structure are easily replaceable, if necessary. The structure isolates wet and dry portions of the electrode, thus avoiding corrosion.

SUMMARY OF THE INVENTION

An electrode having a retaining ring formed of insulating material. The retaining ring has a rear wall integral with one end of a side wall and contains an opening therein. An inwardly extending lip integral with the other end of the side wall defines a front opening. An inwardly extending flange integral with and extending from the junction of the rear and side walls is generally parallel to and spaced intermediate the lip and the rear wall to define an enlarged height annular groove and a reduced height annular groove adjacent the lip and the rear wall, respectively. A generally planar conductive plate having a first side surface and a second side surface is dimensioned to be inserted in the reduced height groove and retained therein. An electrical connector member is secured to the conductive plate first side surface and extends into the retaining ring rear wall opening. A sponge member has a thickness approximately equal to the height of the enlarged height groove and is positionable in the enlarged height groove, enabling the sponge to be retained therein. The sponge, when wet, is juxtaposed to the conductive plate second side surface and extends into the front wall opening.

The advantages of this invention, both as to its construction and mode of operation, will be readily appreciated as the same becomes better understood by reference to the following detailed description when considered in connection with the accompanying drawings in which like reference numerals designate like parts throughout the Figures.

DESCRIPTION OF THE PREFERRED EMBODIMENTS

Figure 1:
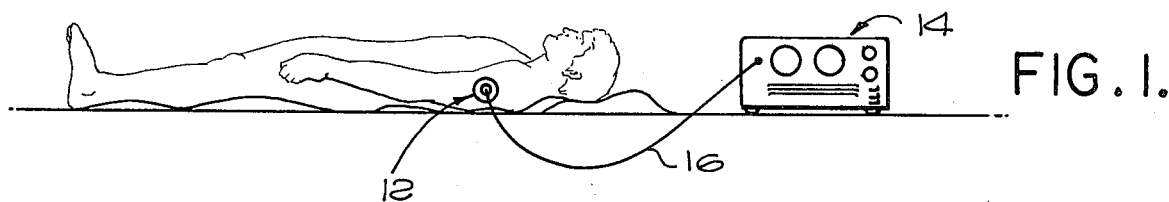
FIG. 1 is a perspective view illustrating a typical use of the electrode of the invention.

Referring now to the drawings, there is illustrated in FIG. 1 an electrode 12 constructed in accordance with the principles of the invention and used in a typical operational configuration. As shown in FIG. 1, the electrode is placed on the arm of a person for transmitting electrical signals from a signal generator 14. A lead 16 interconnects the signal generator 14 to the electrode 12. Typically, the signal generator may be of the type described in my co-pending U.S. Pat. Ser. No. 583,872 filed June 5, 1975 and entitled "Apparatus for Generating Applied Electrical Stimuli Signals". In normal operation as described in my co-pending patent application, low current electrical pulse signals are transmitted to the body to stimulate the body nerves with the resultant effect that pain and/or certain circulatory difficulties are relieved and the body function will attempt to return to normal.

Figure 2:
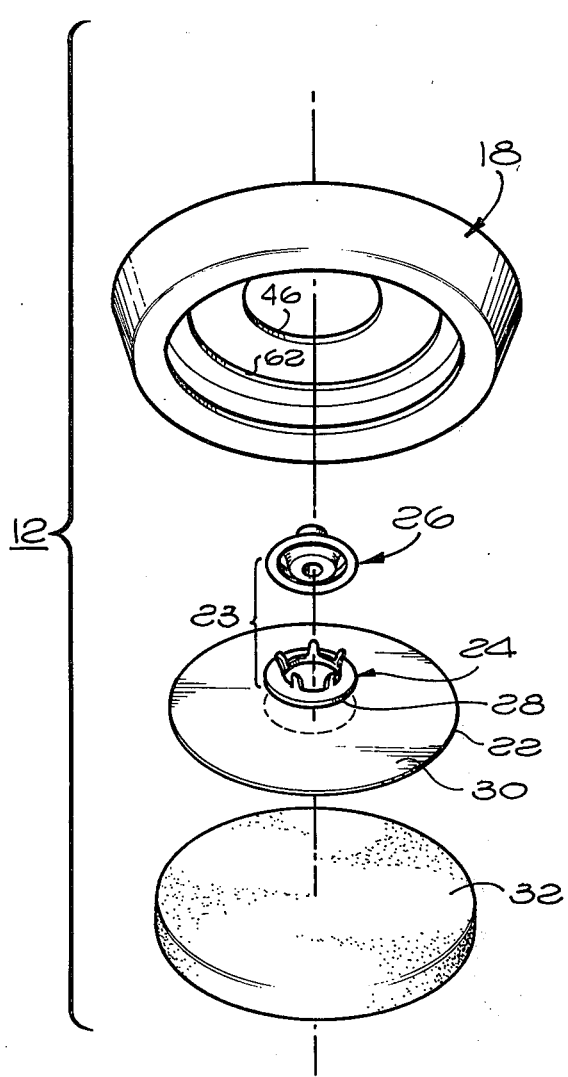
FIG. 2 is an exploded perspective view of the electrode of FIG. 1.

As shown in greater detail in FIG. 2 in an exploded configuration, the electrode 12 comprises a retaining ring 18 made of insulative material. Preferably, the retaining ring 18 may be molded from urethane which is flexible when formed in thin sections. Alternatively, of course, other flexible insulative material can be used for the retaining ring 18. A conductive plate 22 formed of stainless steel is positioned in the retaining ring. The conductive plate 22 could be formed of other conductive materials as well. A two-piece connector 23 formed of a fastener 24 and a contact body 26 is positioned on the conductive plate 22 with the fastener base 28 being soldered with low temperature silver solder or otherwise electrically secured to the conductive plate first side surface 30. The two-piece connector 23 will be described in greater detail hereinafter. Additionally, a sponge 32 is positioned in the retaining ring 18.

Figure 3:
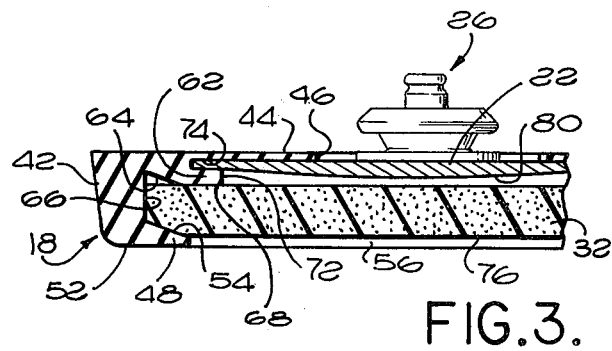
FIG. 3 is a partial cross-sectional view of the electrode of FIG. 2.

Referring now to FIG. 3 the electrode 12 is shown in assembled cross-sectional view illustrating the detailed components thereof. The retaining ring 18 is formed of a side wall 42 which is integrally molded with a rear wall 44 extending inwardly from the rear end of the side wall 42. The rear wall 44 contains an opening 46 having a diameter greater than that of the contact body 26.

The front end of the retaining ring 18 contains an inwardly extending lip 48 whose front surface 52 is flush with the front end of the side wall 42. The interior surface 54 of the lip 48 extends at an angle from the edge 56 of the lip towards the side wall 42, thus giving the lip a generally triangular cross-sectional configuration.

An inwardly extending flange 62 extends from the interior junction of the side wall 42 and the rear wall 44. The flange 62 interior surface 64 extends from the junction of the side wall 42 and the end wall 44 at an angle whose plane is generally parallel to the angle of the lip surface 54 so as to define a groove 66 between the lip surface 54 and the flange surface 64. At approximately the plane of the lip edge 56 the surface 64 is integrally formed with a flange surface 68 which is formed in a plane parallel to the rear wall 44. The flange 62 then terminates at an edge 72 which is intermediate to the plane of the lip 56 and the rear opening 46. A reduced height groove 74 is formed intermediate the flange 62 and the rear wall 44. The reduced height groove 74 extends to approximately to the lip edge 56.

Figure 4:
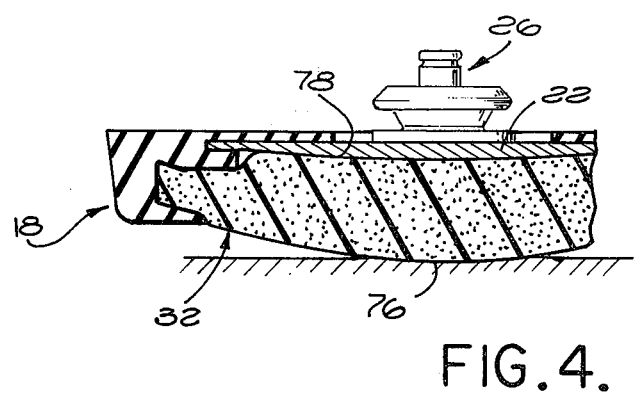
FIG. 4 is a partial cross-sectional view of the electrode of FIG. 2 in an operational mode.

In assembly, the conductive plate 22 has a diameter approximately equal to the diameter of the groove 74 and when inserted therein forms a seal therewith. The conductive plate 22 is inserted so that the connector contact body 26 extends into the opening 46 of the rear wall 44. The sponge 32 is then inserted into the groove 66 with the edge of the sponge abutting the interior surface of side wall 42. As can be seen in FIG. 4, when the sponge 32 is immersed in a liquid enabling the sponge to be conductive, the ends of the sponge adjacent the side wall tend to fill the groove 66 intermediate the parallel walls 54 and 64 of the lip 48 and the flange 62, respectively. The angular configuration of surfaces 54 and 64 is normally chosen to be parallel to the front surface of the conductive sponge as it extends beyond the front of the lip surface 52. The rear surface of the sponge 78 when immersed in a liquid expands to that it is juxtaposed with an outwardly bowed portion of the conductive plate second side surface 80. The groove 66 is thus designed to secure the sponge 32 in the retaining ring 18 while both dry and wet. Electrical signals which are connected through the lead 16 to the conductive plate through the connector can be transmitted through the conductive sponge to the surface of a body. Simultaneously, the seal formed by the conductive plate in the groove 74 separates the wet and dry portion of the electrode structure. Further, the rear opening 46 in the end wall 44 enables moisture adjacent to the electrical connector 23 to be removed by ventilation.

Figure 5:
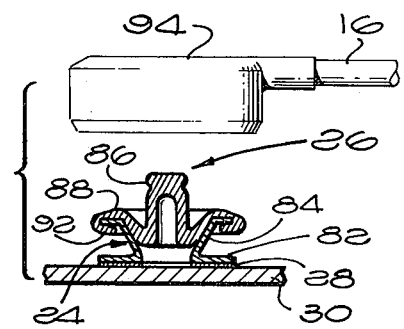
FIG. 5 is a partial cross-sectional view of the electrode of FIG. 2 illustrating the interconnection of the electrode connector and the electrode of FIG. 2.

Referring now to FIG. 5, the connector 23 structure is shown in greater detail. The fastener 24 is formed of a ring 82 whose base 28 is soldered to a surface of the conductive plate 22. Upwardly extending prongs 84 extend from the interior edge of the ring 82. The contact body 26 contains a central pin portion 86. An outwardly extending flange 88 tapers from one end of the pin 86 and terminates at an inwardly extending lip 92. After the fastener 24 has been soldered to the plate 22, the contact body is positioned so that the prongs 84 are secured intermediate the flange 88 and the lip 92. The two-piece configuration of the connector enables the fastener 24 to be heated when soldered to the conductive plate, while minimizing damage to the contacting body 26 surface, as it is secured to the fastener after the soldering has been completed.

The lead 16 may contain a conventional socket contact 94. The socket contact 94 is crimped or soldered to one end of the lead 16 enabling electrical signals to be coupled from the transmitter 14 of FIG. 1 when the socket contact 94 is mated with the pin 86 of the connector 23. While the electrode structure has been illustrated as being circular in configuration, it should be noted that the other shapes such as elliptical or rectangular could be used as well.

I claim:
1. An electrode comprising:
a retaining ring formed of insulating material and having a side wall and a rear wall integral with one end of said side wall with an opening formed in said rear wall, an inwardly extending lip integral with the other end of said side wall defining a front opening;
an inwardly extending flange integral with and extending generally from the junction of said rear and side walls, said flange being generally parallel to and spaced intermediate said lip and said rear wall to define an enlarged height annular groove and a reduced height annular groove adjacent said lip and said rear wall, respectively;
a generally planar conductive plate in said reduced height groove having a first side surface and a second side surface and having dimensions for enabling said plate to be inserted in said reduced height groove and retained therein;
an electrical connector being secured to said conductive plate first side surface and extending into the retaining ring rear wall opening;
a sponge member having a front surface and a rear surface, said sponge member having a thickness approximately equal to the height of said enlarged height groove
wherein said sponge member is retained in said enlarged height groove, said sponge member when wet having said rear surface juxtaposed with said conductive plate second side surface and said front surface extending into said front opening; and
said enlarged height annular groove being formed of a pair of spaced apart surfaces on said lip and said flange, respectively, said spaced apart surfaces being formed in planes having an angle which intersects the plane of said planar conductive plate, said spaced apart surface planes being generally parallel to the plane of said sponge member front surface when said sponge member is immersed in a liquid.

* * * * *